US009820937B2

(12) United States Patent
Brewer et al.

(10) Patent No.: US 9,820,937 B2
(45) Date of Patent: Nov. 21, 2017

(54) PHARMACEUTICAL COMPOSITION FORMULATED FOR PRE-GASTRIC ABSORPTION OF MONOAMINE OXIDASE B INHIBITORS

(75) Inventors: Francesca Mary Brewer, Slough (GB); Edward Stewart Johnson, Berkshire (GB); Anthony Clarke, Oxfordshire (GB)

(73) Assignee: R.P. Scherer Technologies, LLC, Somerset, NJ (US)

( * ) Notice: Subject to any disclaimer, the term of this patent is extended or adjusted under 35 U.S.C. 154(b) by 976 days.

(21) Appl. No.: 12/782,584

(22) Filed: May 18, 2010

(65) Prior Publication Data
US 2010/0227933 A1 Sep. 9, 2010

Related U.S. Application Data

(63) Continuation of application No. 10/957,947, filed on Oct. 4, 2004, now abandoned, which is a continuation-in-part of application No. 10/610,613, filed on Jul. 1, 2003, now abandoned, which is a continuation of application No. 08/894,764, filed on Nov. 17, 1997, now abandoned.

(51) Int. Cl.
*A61K 31/137* (2006.01)
*A61K 9/20* (2006.01)
*A61K 9/00* (2006.01)
*A61K 31/136* (2006.01)

(52) U.S. Cl.
CPC .......... *A61K 9/0056* (2013.01); *A61K 31/136* (2013.01); *A61K 31/137* (2013.01); *A61K 9/2095* (2013.01)

(58) Field of Classification Search
None
See application file for complete search history.

(56) References Cited

U.S. PATENT DOCUMENTS 5,017,607 A * 5/1991 Chiesi .......................... 514/534
6,117,912 A * 9/2000 DiSanto ...................... 514/654

FOREIGN PATENT DOCUMENTS

WO WO 96/26714 A1 * 9/1996

OTHER PUBLICATIONS

Boulmedarat et al. "Evaluation of Buccal Methyl-Beta-Cyclodextrin Toxicity on Human Oral Epithelial Cell Culture Model." Journal of Pharmaceutical Sciences. 94(6); 2005:1300-1309.*
"Deprenyl". Monograph 2893. The Merck Index (Eleventh Edition). Merck & Co., Inc. 1989. p. 458.*

* cited by examiner

*Primary Examiner* — L. R. Draper
(74) *Attorney, Agent, or Firm* — Stroock & Stroock & Lavan LLP

(57) ABSTRACT

The invention described herein provides a fast dispersing oral solid dosage form containing monoamine oxidase B inhibitor (MAO-B inhibitor) as the active ingredient, and method of treating disease therewith, such as Parkinson's disease. In one embodiment, the monoamine oxidase B inhibitor selegiline or its analog can be the sole active ingredient in the composition administered. The dosage form composition is formulated to promote absorption through the buccal, sublingual, pharyngeal and/or esophageal mucous membrane tissue, such that at least 5% of the active ingredient is absorbed within one minute of placement in the oral cavity, as determined by a buccal absorption test. Monoamine oxidase B inhibitor compounds administered in accordance with the invention decrease the amount of undesirable metabolites associated with first pass effect of selegiline, for example, such as amphetamine and methamphetamine. The invention provides a number of other advantages over conventional orally administered tablet forms, including administration of monoamine oxidase B inhibitor compounds to patients that have difficulty swallowing.

18 Claims, 10 Drawing Sheets

Plasma Selegiline AUC∞ and $C_{max}$ Values and 24 Hour Urinary Excretion of β-Phenylethylamine(PEA) following Administration of Single Doses of Zydis Selegiline 1.25mg (Combined Data from Z/SEL/95/003 and Z/SEL/95/023) and 10mg of Marketed Tablets of Selegiline (Combined Data from All Studies)

|  |  | Zydis Selegiline 1.25mg | Marketed Tablets 10mg |
|---|---|---|---|
| AUC ∞ (ng.h/mL) | Mean | 0.75 | 1.11 |
|  | SD | 0.56 | 1.45 |
|  | n | 35 | 81 |
|  | Range | 0.16 to 2.69 | 0.09 to 6.82 |
| $C_{max}$(ng/mL) | Mean | 1.55 | 1.22 |
|  | SD | 1.07 | 1.82 |
|  | n | 35 | 81 |
|  | Range | 0.32 to 4.58 | 0.07 to 8.76 |
| 24 Hour Urinary Excretion Of PEA (μg) | Mean | 14.09 | 23.42 |
|  | SD | 12.05 | 26.25 |
|  | n | 35 | 58 |
|  | Range | 1.87 to 61.63 | 0.86 to 115.49 |

FIG-9

PHARMACEUTICAL COMPOSITION FORMULATED FOR PRE-GASTRIC ABSORPTION OF MONOAMINE OXIDASE B INHIBITORS

CROSS-REFERENCE TO RELATED APPLICATIONS

This application is a continuation of U.S. patent application Ser. No. 10/957,947, entitled "Pharmaceutical Composition Formulated for Pre-Gastric Absorption of Monoamine Oxidase B Inhibitors," filed Oct. 4, 2004, now abandoned, which is a continuation-in-part of U.S. patent application Ser. No. 10/610,613, filed Jul. 1, 2003, now abandoned, which is a continuation of U.S. patent application Ser. No. 08/894,764, filed Nov. 17, 1997, now abandoned, which is the U.S. national filing of International patent application No. PCT/GB96/00484 (WO 96/26720 published Sep. 6, 1996) with an international filing date of Mar. 1, 1996, which claims benefit of priority to Great Britain Patent Application No. 9504235.4 filed Mar. 2, 1995 and Great Britain Patent Application No. 9517063.5 filed Aug. 18, 1995, the entire disclosure of each of which is expressly incorporated by reference herein.

FIELD OF THE INVENTION

The invention relates to a pharmaceutical composition for the treatment of diseases such as Parkinson's disease. In particular, the invention pertains to a fast disintegrating oral solid dosage form containing monoamine oxidase B inhibitor compounds as the active ingredient, and methods of treatment therewith.

BACKGROUND OF THE INVENTION

Selegiline, or (−)-N,α-dimethyl-N-2-propynyl-phenethylamine, is known to be useful in the treatment of Parkinson's disease. The mechanism of action of selegiline has not been fully elucidated. Selegiline, however, is a potent irreversible inhibitor of monoamine oxidase, with a greater affinity for the type B form of the enzyme. Monoamine oxidase is known to play an important role in the breakdown of biological amines, such as dopamine, noradrenaline and 5-hydroxytryptamine (serotonin) in the brain. It is thought that the inhibition of monoamine oxidase type B (MAO-B) may lead to enhancement of the effects of dopamine and phenethylamine in the brain of patients with Parkinson's disease, thus leading to improved control of movement. See for example, Gaal and Hermez, *Inhibitors of Monoamine Oxidase B, Pharmacology and Clinical Use in Neurodegenerative Disorders*, (edited by I. Szelenyi, Birkhauser Verlag, Basel, Switzerland), Chapter 4 (1993) (hereinafter referred to as Szelenyi).

Selegiline is currently administered orally in the form of conventional tablet design and to be swallowed whole. Alternatively, selegiline is also administered in a measure amount of syrup for rapid swallowing. Accordingly, selegiline administered this way is absorbed from the gastrointestinal tract, that is, the stomach, small intestine and the proximal large intestine (colon), into the hepatic portal system and is presented to the liver before reaching systemic circulation.

One problem associated with the administration of conventional tablet forms of selegiline is that the liver is known to be the principal site for conversion of active selegiline into metabolites, some of which are undesirable. Consequently, this first pass of absorbed selegiline through the liver results in extensive metabolism of the drug, and a significant proportion of the absorbed dose of intact selegiline never reach systemic circulation or, therefore, the brain. This phenomenon is generally known as the "first pass effect", and results in a decrease in the bioavailability of selegiline administered in the conventional manner. See, for example, Heinonen et al., *Clinical Pharmacology & Therapeutics*, Vol. 56, No. 6 (1994), pp. 742-749.

Another problem with conventional selegiline is its undesired metabolites. It is known that selegiline is metabolized to produce N-desmethylselegiline, methamphetamine and amophetamine according to the following metabolic pathway:

Selegiline

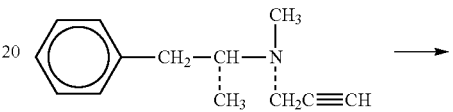

Selegiline

L-(-)-Desmethylselegiline

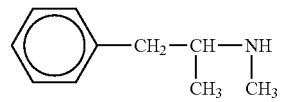

L-(-)-Methamphetamine

L-(-)-Desmethylselegiline

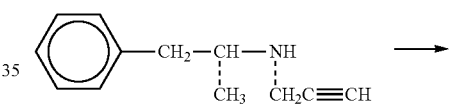

L-(-)-Desmethylselegiline

L-(-)-Amphetamine

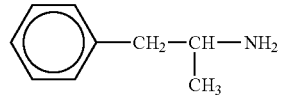

L-(-)-Amphetamine

Although it has been suggested that N-desmethylselegiline may contribute to the desired inhibition of monoamine oxidases (see, for example, Heinonen et al. in Chapter 10 of Szelenyi), methamphetamine and amphetamine exhibit no useful effect in Parkinson's disease. Indeed, since methamphetamine and amphetamine are both stimulants of the central nervous system and of the heart, their presence produces undesirable side-effects such as insomnia and cardiac arrhythmias. In order to minimize the central nervous system stimulant effect, currently available dosage forms of selegiline must be administered by no later than mid-day so that the unwanted stimulant effect will subside at the end of the day. Clearly, this situation is far from satisfactory.

Yet another problem associated with conventional selegiline administration is that which is associated with its co-administration with levodopa. Co-administration of selegiline with levodopa has even been associated with fatalities, and unadjusted (unreduced) amounts of levodopa can cause dyskenesias (defects in the ability to perform voluntary movement).

Yet another undesired side-effect of conventional selegiline administration is orthostatic hypotension and syncope is some patients, which has been linked to non-selective MAO inhibition. Conventional selegiline can also cause undesirable and capricious side effects due to sudden changes in plasma concentration of selegiline itself and/or its known metabolites. The presence or absence of food in the digestive tract may also contribute to the unpredictability.

One analogue of selegiline, para-fluoroselegiline, is also a monoamine oxidase B inhibitor and exhibits very similar pharmacological activity to that of selegiline. Many other compounds, some of which are not chemically related to selegiline, also have monoamine oxidase B-inhibiting properties. A number of these have also demonstrated utility for treatment of Parkinson's disease, treatment of depression, and/or treatment or prophylaxis of Alzheimer's disease. Among such MAO-B inhibitors are: lazabemide (N-(2-aminoethyl)-5-chloropyridine-2-carboxamide hydrochloride); rasagiline (2,3-dihydro-N-2-propynyl-1H-inden-1-amine); 2-BUMP (N-(2-butyl)-N-methylpropargylamine); M-2-PP (N-methyl-N-(2-pentyl)-propargylamine); MDL-72145 (beta-(fluoromethylene)-3,4-dimethoxy-benzeneethanamine); and mofegiline (E)-4-fluoro-β-(fluoromethylene) benzene butanamine hydrochloride).

Clinical studies have shown that up to 82% of patients suffering with Parkinson's disease have difficulty swallowing and tend to dribble. Conventional selegiline tablets, syrups, and the like, still require the patient to attempt swallowing. Moreover, conventional tablets need to be administered with water, requiring another difficult swallowing act for such patients.

From a clinical perspective, it would be highly desirable to administer MAO-B inhibitors while enhancing the bioavailability of the active ingredient and avoiding first pass effect and its undesirable metabolites, hence affording a comparatively rapid onset and prolonged duration of effect as compared to conventional administration forms. Even more desirable would be the ability to administer MAO-B in a dosage form that does not present difficulty in ingestion in those patients that have difficulty swallowing, can be handled easily, and affords assurance and greater predictability of its administration and effect.

SUMMARY OF THE INVENTION

The invention provides a pharmaceutical composition as a rapidly disintegrating solid oral dosage form comprising a carrier and monoamine oxidase B inhibitor compound as an active ingredient. It has been discovered that an oral solid pharmaceutical dosage form containing a monoamine oxidase B inhibitor, such as selegiline, can be prepared that permits effective pre-gastric oral administration and avoids the disadvantages associated with conventional swallowed tablet forms of the drug and permits its administration without other active ingredients and their associated risks.

The invention presents a number of significant improvements over conventional selegiline administration. The administration of monoamine oxidase B inhibiting compounds in fast dissolving oral solid dosage form improves ease and convenience of administration for practitioners and patients alike. This is especially the case in dysphagic patients with Parkinson's disease, wherein the invention avoids coordination of sipping water and swallowing the tablet because no water is needed to administer MAO-B inhibitors in the invention.

Further, no advanced preparation, measuring or mixing, etc. is needed. Thus, the inaccuracies of measuring out liquid doses are eliminated. As a solid dosage form, it can still be packaged, handled and manipulated by both caregiver and patient as easily as a conventional tablet.

Surprisingly, it has been discovered that an equivalent efficacy of selegiline can be obtained with oral administration in accordance with the invention as with conventional selegiline tablets by administering a fraction of the amount of the MAO-B inhibitor within the rapid disintegrating solid oral dosage form of the invention.

The invention provides a fast disintegrating oral solid dosage form formulated for pre-gastric absorption of monoamine oxidase B inhibitor, said dosage form comprising a monoamine oxidase B inhibitor and a carrier. Preferred monoamine oxidase B inhibitor compounds that can be used in accordance with the invention include those having the following general formula:

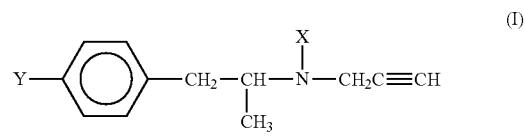

(I)

or acid addition salt thereof, wherein X represents hydrogen or methyl group, and Y represents hydrogen or fluorine. Preferably, Y is hydrogen. In an even more preferred embodiment, X is methyl and Y is hydrogen, which is also known as the MAO-B inhibitor selegiline.

In a preferred embodiment of the invention, the fast disintegrating oral solid dosage form is formulated for pre-gastric absorption such that at least 5% of the active monoamine oxidase B inhibitor is absorbed within one minute of placement in the oral cavity. In an even more preferred embodiment, the dosage form is also formulated to disintegrate within 10 seconds after placement in the oral cavity.

In one embodiment, the invention provides a fast disintegrating oral solid dosage form formulated for pre-gastric absorption wherein the active ingredient consists of selegiline, and said dosage form comprises a carrier.

The invention also provides a method for treatment of Parkinson's disease comprising administering to a patient in need of treatment therefore, a fast dispersing oral solid dosage form formulated for pre-gastric absorption, said dosage form comprising a pharmaceutically effective amount of monoamine oxidase B inhibitor and carrier, said dosage form being formulated for pre-gastric absorption.

The invention further provides a method for treatment or prophylaxis of Alzheimer's disease comprising administering to a patient in need of treatment thereof a fast disintegrating oral solid dosage form formulated for pre-gastric absorption comprising a pharmaceutically effective amount of monoamine oxidase B inhibitor and carrier, wherein said dosage form is formulated for pre-gastric absorption.

Further provided is a method for treatment or prophylaxis of depression comprising administering to a patient in need of said treatment a fast disintegrating oral solid dosage form containing a pharmaceutically effective amount of monoamine oxidase B inhibitor and carrier, said dosage form being formulated for pre-gastric absorption.

Another method of increasing the level of phenethylamine in the body comprising administering to a patient in need of said treatment a fast disintegrating oral solid dosage form containing a pharmaceutically effective amount of monoamine oxidase B inhibitor and carrier, said dosage form being formulated for pre-gastric absorption.

Other advantages associated with the invention will become apparent from the following description.

BRIEF DESCRIPTION OF THE DRAWINGS

FIG. 9 is a table containing comparative urinary excretion data for phenethylamine following administration of Zydis® selegiline and commercial selegiline tablet.

DETAILED DESCRIPTION OF THE INVENTION

Figure 1:
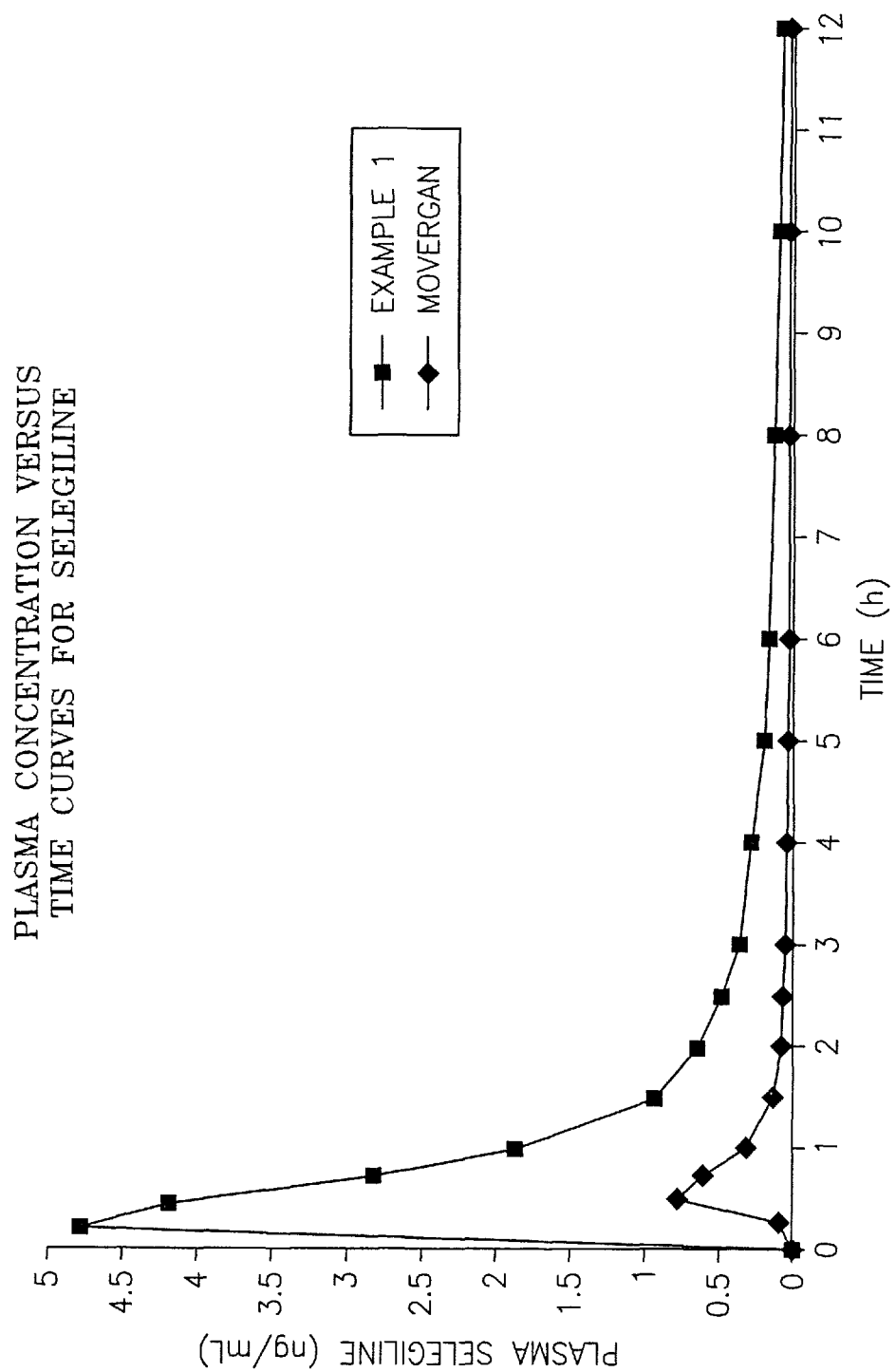
FIG. 1 is a graph showing plasma concentration versus time curve for the specific compound selegiline.

As used herein, the phrase "pre-gastric absorption" is meant to refer to absorption of the active ingredient from that part of the alimentary canal prior to the stomach, and includes buccal, sublingual, oropharyngeal and esophageal absorption.

According to the invention, the composition is formulated such that pre-gastric absorption of the monoamine oxidase B inhibitor occurs primarily across the mucous membranes in the mouth, pharynx and esophagus. It is therefore preferred that the composition of the invention be formulated which sustains the active ingredient in contact with the buccal, sublingual, pharyngeal and/or esophageal mucous membranes.

Pre-gastric absorption of MAO-B inhibitors can be assessed using the method described for selegiline in Example 3 below. This test is similar to the "buccal absorption test" cited by Harris and Robinson, *J. Pharm. Sci.*, Vol. 81 (1992), p. 1-10, as a well-recognized method for evaluating buccal absorption of drugs. Thus, the test formulation containing the clinically effective dose of the MAO-B inhibitor is retained in the mouth for one (1) minute before it is expectorated. The mouth is then rinsed with 3 aliquots of 25 ml water, which are then similarly expectorated. The total amount of MAO-B inhibitor is then determined from the expectorated mouth washings using a suitable analytical technique, such as HPLC. The recovered quantity of MAO-B inhibitor is subtracted from the total amount of drug initially placed in the mouth to determine the total amount of the drug which has been pre-gastrically absorbed. For significant buccal absorption to have occurred, it is generally preferred that at least 5% of the MAO-B inhibitor be absorbed in one (1) minute in this test, more preferably at least 10% is absorbed in one (1) minute and most preferably at least 15% of the MAO-B inhibitor within one (1) minute.

Fast-Disintegrating Oral Solid Dosage Forms

As used herein, the terms "fast dissolving", "fast disintegrating", "rapid dissolving", "rapid disintegrating" when used to describe the dosage form are meant to refer to the property of the solid form disintegrating or dissolving upon placement within the oral cavity (and saliva contact) within a relatively shortened time period of about 60 seconds.

A variety of fast-dispersing solid dosage forms can be used in accordance with the invention. One example of such a dosage form is described in U.S. Pat. No. 4,855,326. This reference describes a melt spinnable carrier agent, such as sugar, that is combined with an active ingredient and spun into a resultant "candy floss" preparation. The spun "candy floss" is the compressed into a rapidly dispersing, highly porous solid dosage form.

U.S. Pat. No. 5,120,549 describes a fast-dispersing matrix system which is prepared by first solidifying a matrix-forming system dispersed in a first solvent and subsequently contacting the solidified matrix with a second solvent that is substantially miscible with the first solvent at a temperature lower than the solidification point of the first solvent, the matrix-forming elements and active ingredient being substantially insoluble in the second solvent. Upon substantial removal of the first solvent, a fast-dispersing matrix results.

U.S. Pat. No. 5,079,018 describes a fast dispersing dosage form which comprises a porous skeletal structure of a water soluble, hydratable gel or foam material that has been hydrated with water, rigidified in the hydrated state with a rigidifying agent and dehydrated with a liquid organic solvent at a temperature of about 0° C. or lower to leave spaces in place of hydration liquid.

Published International Application No. WO 93/12769 (PCT/JP93/01631) describes a fast dispersing dosage form of very low density formed by gelling, with agar, aqueous systems containing the matrix-forming elements and active ingredient, and then removing water by forced air or vacuum drying.

U.S. Pat. No. 5,298,261 describes a fast-dispersing dosage form comprising a partially collapsed matrix network that has been vacuum-dried above the collapse temperature of the matrix. However, the matrix is preferably at least partially dried below the equilibrium freezing point of the matrix.

Published International Application No. WO 91/04757 (PCT/US90/05206) describes a fast dispersing dosage form that contains an effervescent disintegration agent designed to effervesce on contact with saliva to provide rapid disintegration of the dosage form and dispersion of the active ingredient in the oral cavity.

Compositions of then invention can be prepared using processes for preparing the fast dispersing oral solid dosage form, in which the carrier is associated with the active monoamine oxidase B inhibitor compound, utilizing the procedures set forth in the above references, the entire texts of which are again incorporated herein by reference.

Particularly preferred, however, is the dosage form of the type described in UK Patent No. 1,548,022. The dosage form described therein comprises a network of the active ingredient and a water-soluble or water-dispersible carrier which is inert toward the active ingredient. The network is prepared by subliming a solvent from the composition in solid state, wherein the composition comprises the active ingredient and a solution of the carrier in a solvent. When oral solid dosage forms are prepared in accordance with this technique, the composition can disintegrate within 1 to 10 seconds, particularly within 2 to 8 seconds, of being placed in the oral cavity. The texts of all of the above references are incorporated herein by reference.

When the preferred fast dispersing oral solid dosage form is used, the composition preferably contains, in addition to the active ingredient monoamine oxidase-B inhibitor, matrix forming agents and secondary components. Suitable matrix forming agents for use in the invention include materials derived from animal or vegetable proteins, such as gelatins, dextrins and soy, wheat and psyllium seed proteins; gums such as acacia, guar, agar and xanthan; polysaccharides; alginates; carboxymethylcelluloses; carrageenans; dextrans; pectins; synthetic polymers, such as polyvinyl pyrrolidone; and polypeptide/protein or polysaccharide complexes such as gelatin-acacia complexes.

Other matrix forming agents suitable for use in the invention include sugars, such as mannitol, dextrose, lactose, galactose and trehalose; cyclic sugars such as cyclodextrin; inorganic salts such as sodium phosphate, sodium chloride and aluminum silicates; amino acids having from 2 to 12 carbon atoms such as a glycine, L-alanine, L-aspartic acid, L-glutamic acid, L-hydroxyproline, L-isoleucine, L-leucine and L-phenylalanine.

In preparing the composition, one or more matrix forming agents can be incorporated into the solution or suspension prior to solidification. The matrix forming agent can be present in addition to, or to the exclusion of, a surfactant. Aside from forming the matrix, the matrix forming agent may aid in maintaining the dispersion of the active ingredient within the solution or suspension. This is especially advantageous in the case of active agents that are not sufficiently soluble in water and, therefore, must be suspended rather than dissolved.

Secondary components can also be incorporated into the composition of the invention. Suitable secondary components include preservatives, antioxidants, surfactants, viscosity enhancers, coloring agents, flavoring agents, pH modifiers, sweeteners and taste masking agents. Coloring agents that can be used include red, black and yellow iron oxides, and FD&C dyes such as FD&C blue no. 2 and FD&C red no. 40 (available from Ellis & Edward). Flavoring agents that can be used include mint, raspberry, licorice, orange, lemon, grapefruit, caramel, vanilla, cherry and grape flavors, and combinations thereof. Suitable pH modifiers that can be used include citric acid, tartaric acid, phosphoric acid, hydrochloric acid and maleic acid. Sweeteners that can be used include aspartame, acesulfame K and thaumatin. Suitable taste masking agents include sodium bicarbonate, ion exchange resins, cyclodextrin inclusion compounds, adsorbates and microencapsulated actives.

The fast dispersing oral solid dosage form of the invention comprises a monoamine oxidase B inhibitor compound (MAO-B inhibitor) as the active ingredient within the pharmaceutical composition component. Preferred monoamine oxidase B inhibitor compounds for use in the invention are those having the following general formula:

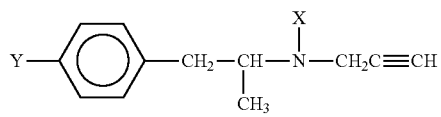

(I)

or an acid addition salt thereof, wherein X represents hydrogen or methyl group, and Y represents hydrogen or fluorine. Preferably, Y is hydrogen. In a preferred embodiment, X is methyl and Y is hydrogen, or in other words, the active MAO-B inhibitor compound is selegiline.

Selegiline or para-fluoroselegiline which is absorbed by pre-gastric absorption from a composition prepared in accordance with this invention passes straight into the systemic circulatory system, thereby avoiding first pass metabolism in the liver. Accordingly, the initial rapid production of unwanted metabolites is reduced, and the bioavailability of active selegiline or para-fluoroselegiline is increased. This produces a number of advantages. For example, the increased bioavailability of selegiline or para-fluoroselegiline means that the dose amount of selegiline or para-fluoroselegiline can be reduced while producing the same or similar beneficial therapeutic effect as compared to conventional oral administration means. Further, there is a decrease in the amount of unwanted MAO-B inhibitor metabolites. In the case of selegiline, this means a reduction in the stimulatory effect of methamphetamine and amphetamine on the central nervous system and heart. Consequently, no restrictions on administration or dosage timing are required for compositions of the invention.

According to the invention, a therapeutically effective amount of monoamine oxidase B inhibitor is present in the dosage form. By the phrases "pharmaceutically effective" and "therapeutically effective", it is meant that the amount of active ingredient to be administered is known to provide the desired effect with respect to the intended treatment in accordance with pharmacological standards, principles and/or research. In the case of selegiline and its analogues of Formula I above, the active ingredient is preferably present in an amount ranging from about 1 to about 30% by weight of the composition. Preferably, the active ingredient is present in an amount of from 1% to about 20% of the composition. In is also preferred that the active ingredient is present in the composition in an amount of from about 0.25 mg to about 30 mg, more preferably 0.50 mg to about 10 mg and, especially preferred, an amount from 1 to 5 mg. In the case wherein other MAO-B inhibitors are used, the active ingredient can be formulated in concentrations and amounts which are likewise clinically effective.

The invention includes a method of treating Parkinson's disease comprising administering to a patient in need of treatment thereof, the fast dispersing oral solid dosage form comprising monoamine oxidase B inhibitor compound as the active ingredient present in a pharmaceutically effective amount, and a carrier. In another aspect of the invention, the method of treatment by administering the composition of the invention can be performed using a composition containing an active ingredient consisting essentially of a monoamine oxidase B inhibitor, e.g., selegiline or a selegiline analogue alone, without the co-administration of a second or other active ingredient for said treatment. This is one of the important advantages associated with the invention.

Treatment of Depression

As mentioned above, selegiline and para-fluoroselegiline are both inhibitors of monoamine oxidase B. The preferred substrate for monoamine oxidase B is phenethylemine—a chemical which occurs naturally in the brain. Phenethylemine is structurally very similar to amphetamine, and recent studies have indicated that phenethylaine can act as a neuromodulator promoting elevation of mood. This is borne out of the fact that patients suffering from depression have been found to have sub-normal levels of phenethylamine in the brain.

In view of these findings, it has been suggested that monoamine oxidase B inhibitors, such as selegiline, may be useful in the treatment of depression, since the inhibition of monoamine oxidase B produces increased levels of phenethylamine. In conventional practice, however, it has generally been found that high doses, typically 30 to 60 g per day for long periods (e.g., 6 weeks) or selegiline are required to elevate mood in depressed patients. Such high doses are associated with non-specific inhibition of monoamine oxidase A and B, whereas selective inhibition of monoamine oxidase B occurs at low doses (e.g., 10 mg or less) of selegiline. Although monoamine oxidase A has very little effect on the metabolism of phenethylamine, it has been suggested that inhibition of monoamine oxidase A may produce an anti-depressant effect by inhibiting deamination of norepinephrine and 5 hydroxytryptamine (serotonin), deficits of which are also associated with depression. However, inhibition of monoamine oxidase A can produce undesirable cardiovascular effects and tyramine-induced hypertensive crisis (the so-called "cheese effect"). Accordingly, the use of such high doses of selegiline or other MAO-B inhibitors to combat depression is clearly far from ideal.

Alternatively, administration of lower doses of selegiline (10 mg or less) in conjunction with phenylalanine (250 mg) (dietary precursor to phenethylamine) has been proposed. In this combination, selegiline inhibits the production of monoamine oxidase B thereby inhibiting the deamination of phenethylamine, and phenylalanine stimulates phenethylamine synthesis. This results in increased levels of phenethylamine in the brain and, therefore, concomitant elevation of mood. However, two active agents need to be given, and the onset of anti-depressant effect is still slow.

To date, no studies have shown consistent anti-depressant activity using low doses of selegiline by itself using conventional administration. Accordingly, another aspect of the invention is a method of treatment and/or prophylaxis of depression comprising administering to a patient in need of such treatment a fast dispersing oral solid dosage form comprising a pharmaceutically effective amount of monoamine oxidase B inhibitor and carrier. It has now been found that if selegiline, or by implication other monoamine oxidase B inhibitors, are formulated in accordance with the present invention, an increase in the amount of phenethylamine occurs in the body and thereby a good anti-depressant effect can be achieved at dose levels associated with selective inhibition of monoamine oxidase B. Moreover, an earlier onset of effect is likely to be achieved than with existing formulation and, in the case of selegiline, the low dose levels result in lower levels of unwanted metabolites and therefore a reduction in their associated side effects.

Alzheimer's Disease

Another aspect of the invention provides a method for treatment and/or prophylaxis of Alzheimer's disease comprising administering to a patient in need of such treatment a fast dispersing oral solid dosage form containing a therapeutically effective amount of monoamine oxidase B inhibitor and a carrier. Recent studies have also suggested that selegiline and other MAO-B inhibitors have a positive effect in the treatment and/or prophylaxis of Alzheimer's disease, since this condition is also associated with a marked increase in levels of monoamine oxidase B in the brain when compared with age-matched controls. Accordingly, since formulation of selegiline and, by implication other monoamine oxidase B inhibitors, when prepared in accordance with the invention, have been shown to increase bioavailability of the active ingredient, such compositions can be especially effective in the treatment and/or prophylaxis of Alzheimer's disease while minimizing unwanted metabolites and associated side effects.

Since it is well known that patients suffering from Alzheimer's disease may not comply with their treatment regimen cooperatively, for example spitting out tablets, fast dispersing oral solid dosage form of the invention is particularly advantageous because of their rapid disintegration in the mouth reduces the opportunity to eject the complete intact dosage form. Furthermore, since a significant portion of the active ingredient is rapidly absorbed into the body using the dosage form of the invention, a significant amount of the active ingredient can reach systemic circulation even if a portion is expectorated.

The invention is further illustrated by the following examples, none of which are to be construed as necessarily limiting the invention:

EXAMPLES

Example 1 Preparation of a Fast-Dispersing Dosage Form Comprising Selegiline (a) Preparation of Selegiline Hydrochloride 2.0% Dispersion Gelatin (720 g) and mannitol (540 g) were dispersed in a portion of purified water (15.75 kg) by mixing thoroughly in the bowl of a vacuum mixer. The remaining water (1.5 liters) was added under vacuum while mixing using an anchor stirrer. The mix was then heated to 40° C.±2° C. and homogenized for ten minutes. When cooled, a 4500 g portion of the mix was removed into a stainless steel vessel and glycine (360 g) aspartame (90 g), grapefruit flavor (54 g), Opatint™ yellow (54 g), citric acid (90 g) and selegiline hydrochloride (360 g) were then added sequentially to this portion while homogenizing using a bench top homogenizer. The remainder of the mix was transferred into a second stainless steel vessel. The mix was homogenized for ten minutes using a bench top homogenizer to dissolve the drug. Once dispersion of the coloring agent was complete, the homogenized portion of the mix in the first vessel was returned to the mixer bowl together with the mix from the second vessel. The combined mixes were then mixed for at least 20 minutes. The bulk dispersion was then homogenized to ensure that mixing was complete.

(b) Preparation of Selegiline Hydrochloride 5 mg Units 250 mg of the selegiline hydrochloride 2.0% dispersion formed in step (a) above was dosed into each one of a series of pre-formed blister pockets having a pocket diameter of 12 mm. The blister laminate comprised 200 μm PVC/30 μm PE/PVDC 90 g per square meter. The product was frozen immediately in a liquid nitrogen freeze tunnel. The frozen product was then stored below −20° C. for a minimum of 24 hours prior to freeze-drying in a freeze drier using a drying temperature of +20° C. and a chamber pressure of 0.5 mbar. The freeze-dried units were then inspected for the presence of critical defects and the remainder of the batch sealed with lidding foil consisting of paper/foil laminate (20 μm aluminum). Each blister was then coded with a batch number and overwrapped in a preformed sachet by placing the blister in the sachet and sealing the open end of the sachet completely. Each sachet was then labeled with the product name, batch number, date of manufacture and supplier's name.

Each unit dosage form had the following composition:

| Ingredient | Weight (mg) | % by wt of composition |
|---|---|---|
| Purified water USP/EP* | 218.500 | 87.4 |
| Selegiline Hydrochloride | 5.000 | 2.0 |
| Gelatin EP/USNF | 10.000 | 4.0 |
| Mannitol BP/USP | 7.500 | 3.0 |
| Aspartame EP/USN | 1.250 | 0.5 |
| Grapefruit flavor 502.106/A | 0.750 | 0.3 |
| Glycine USP | 5.000 | 2.0 |
| Citric acid EP/USP | 1.250 | 0.50 |
| Opatint ™ AD-22901 yellow | 0.750 | 0.3 |
| Total | 250.000 | 100.0 |

*Signifies removed during the lyophilization process.

Example 2 Comparative Pharmacokinetic Study of Selegiline Dosage Forms

The aim of this experiment was to compare the bioavailability of the selegiline hydrochloride formulation of Example 1 prepared according to the invention, with the commercially available tablet form of selegiline hydrochloride sold under the trademark Movergan™ (available from Asta Medica AG, Weismullerstrasse 45, 6000 Frankfurt am Main, Germany).

An open label, randomized, 2-way crossover, volunteer study was performed as follows. Twenty-four subjects of either sex, aged between 45 and 71 years, giving written informed consent, underwent a thorough medical examination to establish their fitness to participate in the study. Subjects received study treatment in the order dictated by a pre-determined randomization schedule. Subjects were given either the formulation of Example 1, or the Movergan™ formulation. Blood samples for determination of pharmacokinetic parameters were taken at baseline (immediately before drug administration), then after 0.25, 0.5, 0.75, 1, 1.5, 2, 2.5, 3, 4, 5, 6, 8, 10, 12, 24, 48, 72 and 96 hours. The study procedures were repeated two weeks later, when subjects were crossed-over to receive their second drug administration. Selegiline hydrochloride was administered as single 10 mg doses (made up from 2×5 mg tablets) of the formulation of Example 1 or of the Movergan™ formulation.

Assays were performed to determine the concentrations of selegiline, N-desmethylselegiline, methampgetamine, and amphetamine in each of the blood plasma samples. The following pharmacokinetic parameters were determined for all four analyzed substances: bioavailability (as measured as the area under the curve (AUC) of the drug concentrations/time plot), Cmax (the maximum plasma concentration achieved and Tmax (the time point at which Cmax was observed).

Figure 2:
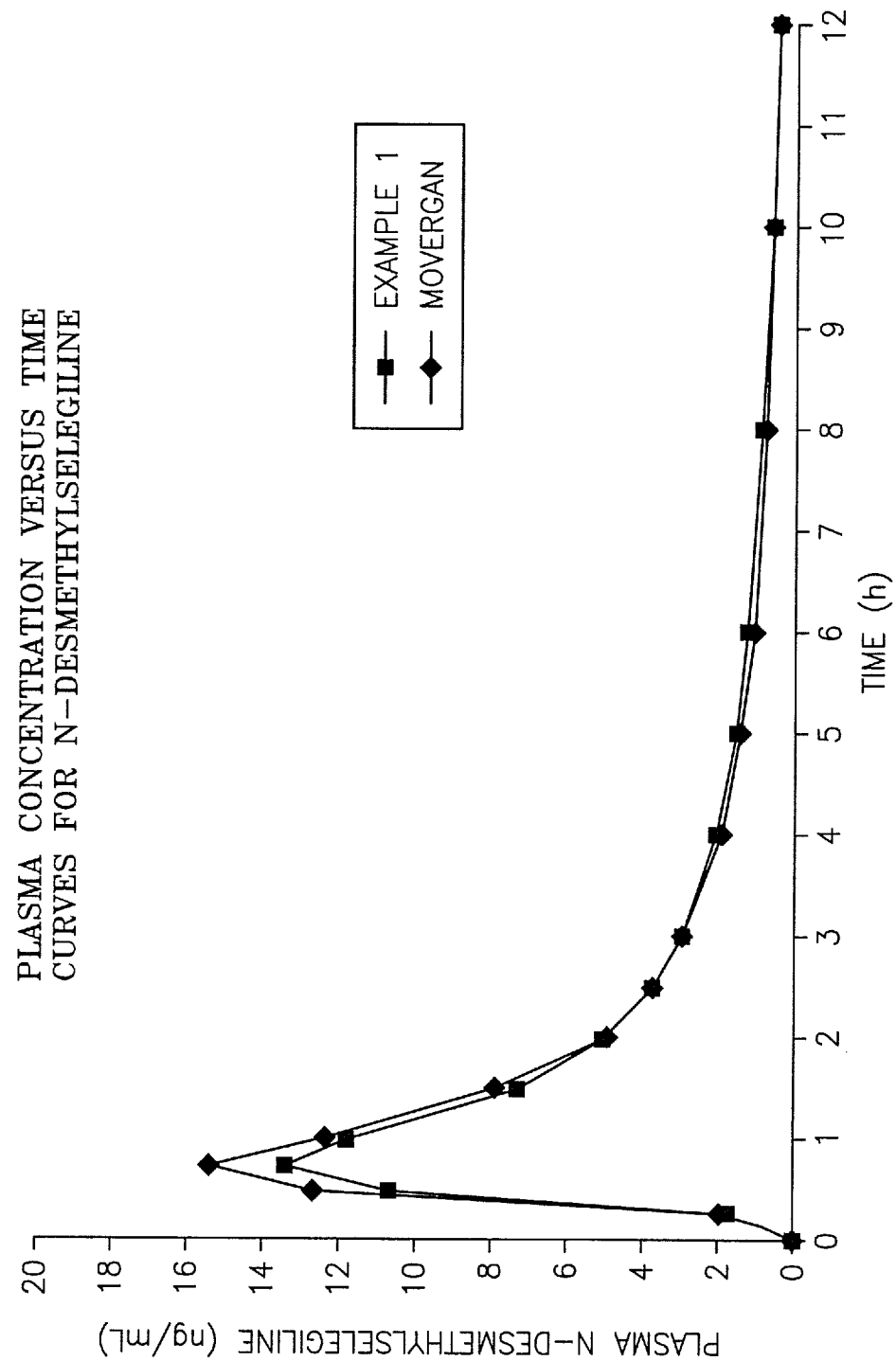
FIG. 2 is a graph showing plasma concentration versus time curve for the specific compound N-desmethylselegiline.
Figure 3:
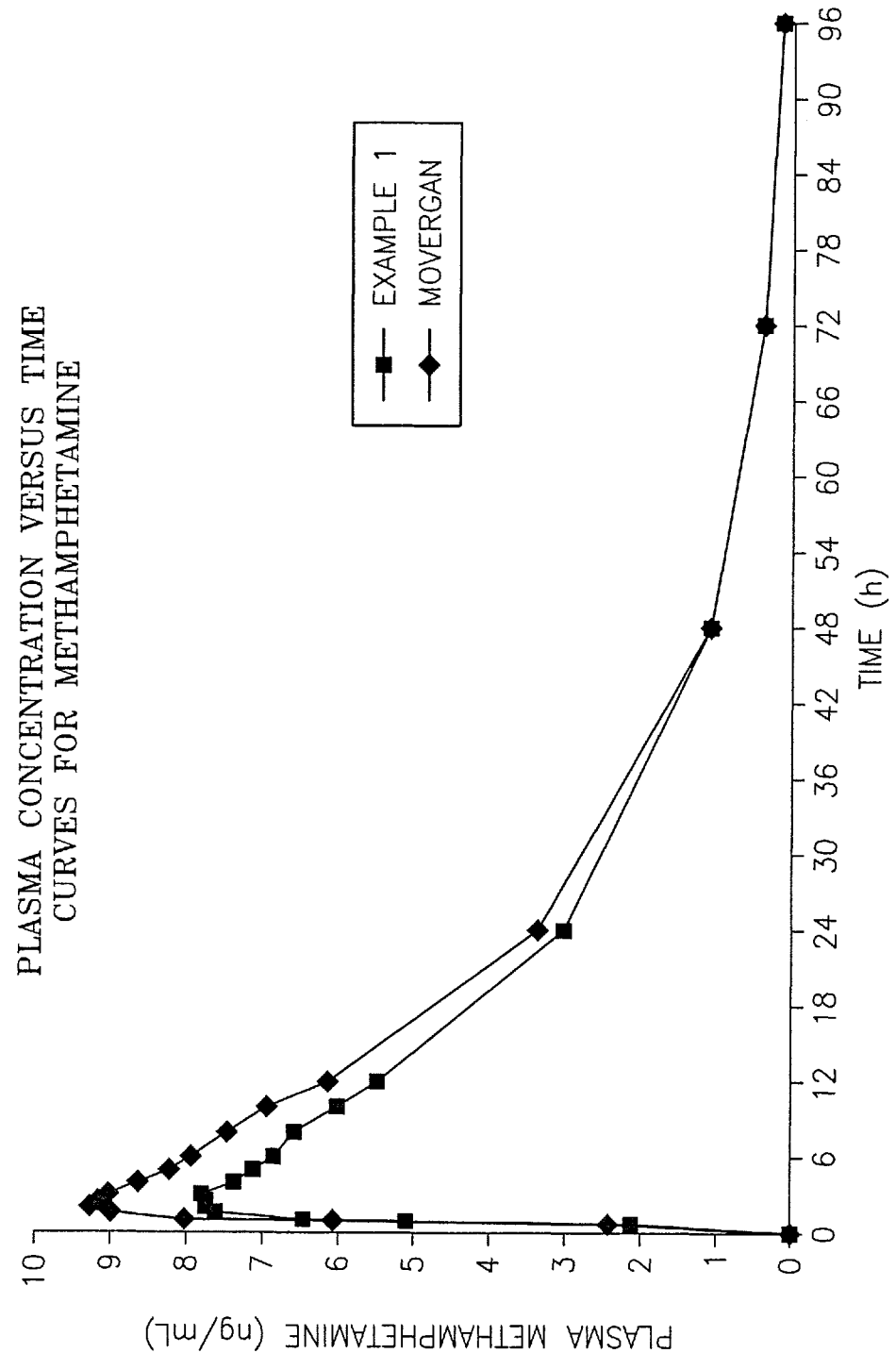
FIG. 3 is a graph showing plasma concentration versus time curve for the specific compound methamphetamine.
Figure 4:
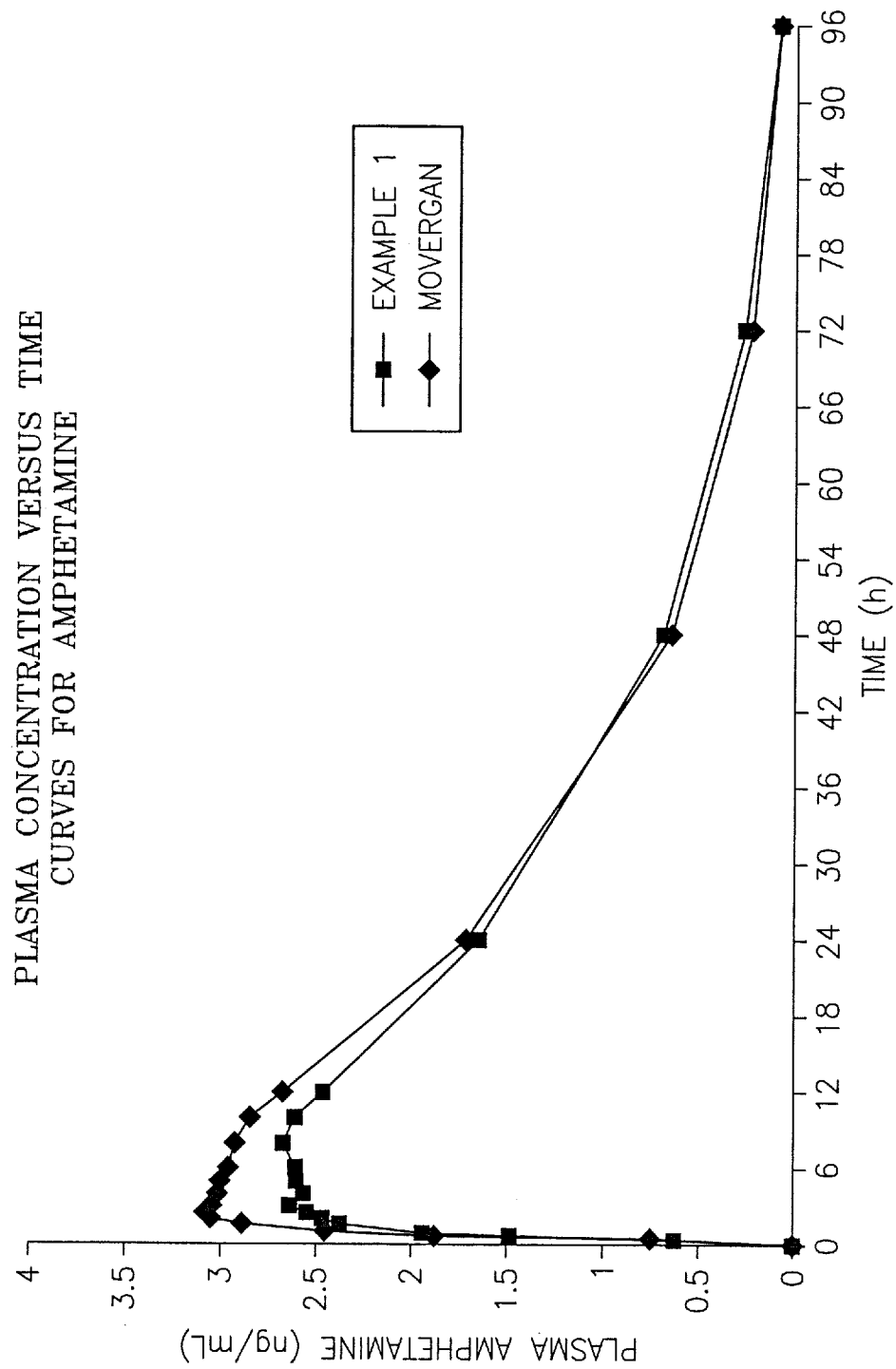
FIG. 4 is a graph showing plasma concentration versus time curve for the specific compound amphetamine.

The results are shown in graphical form in FIGS. 1 to 4 where each figure is a plot of the concentration of a specific compound in a blood plasma sample versus the time at which the sample was taken for the formulation of Example 1, and the tablet formulation sold under the trademark Movergan™. In FIG. 1, the specific compound is selegiline. In FIG. 2, the specific compound is N-desmethylselegiline. In FIG. 3, the specific compound is methamphetamine. In FIG. 4, the specific compound is amphetamine.

The results are shown in numerical form in Table 1 below. In this table, the references to N-desmethylselegiline, methamphetamine and amphetamine are to the L-(−)-isomers of these compounds.

TABLE 1

| | Selegiline | N-desmethyl-selegiline | Metham-phetmine | Amphetamine |
|---|---|---|---|---|
| AUC | | | | |
| Example 1 | 6.93 | 36.58 | 215.43 | 104.85 |
| Movergan ™ | 0.83 | 35.60 | 234.91 | 108.01 |
| Cmax | | | | |
| Example 1 | 5.17 | 14.47 | 8.90 | 3.01 |
| Movergan ™ | 0.86 | 17.36 | 10.59 | 3.54 |
| Tmax | | | | |
| Example 1 | 0.33 | 0.71 | 2.40 | 5.40 |
| Movergan ™ | 0.58 | 0.72 | 2.16 | 4.16 |

Key
AUC = area under the plasma concentration-time curve (ng · h/ml)
Cmax = maximum plasma concentration (ng/ml)
Tmax = time to maximum plasma concentration (h)

Results:

From FIGS. 1 to 4 and Table 1, it is apparent that the bioavailability of selegiline from the formulation of Example 1 is more than eight times that of selegiline from the Movergan formulation, despite the fact that both formulations contained the same amount of active ingredient. Also, the bioavailability of N-desmethylselegiline is very similar to for both formulations. The bioavailability of methamphetamine and amphetamine, which are known not to contribute to the therapeutic effect, are very similar to Example 1 and the Movergan™ formulation. However, in view of the much greater bioavailability of selegiline from the Example 1 formulation, it is envisaged that the dose of selegiline could be significantly reduced thereby significantly reducing the quantity of unwanted central nervous system and cardiac stimulant metabolites and undesired side effects caused by them while still achieving the desired levels of selegiline in plasma and hence the desired therapeutic effect associated with monoamine oxidase B inhibition.

In Table 1, the ratio of the area under the plasma concentration-time curve (AUC) for selegiline and the AUC for N-desmethylselegiline was 0.0233 for the Movergan™ formulation, indicating clearly the extensive metabolism of selegiline when administered in an existing dosage form.

The corresponding AUC ratio for Example 1 in Table 1 was 0.1894. This demonstrates that pre-gastric absorption of selegiline results in a greater proportion of the administered dose being absorbed in the unmetabolized form. It demonstrates further that the selegiline:N-desmethylselegiline AUC ratio can be used as another indicator of the degree of pre-gastric absorption in selegiline-containing compositions in accordance with this invention. It is generally preferred that the ratio of selegiline AUC to the N-desmethylselegiline AUC should be greater than 0.05, more preferably greater than 0.075, and most preferably greater than 0.10.

Example 3 Pre-Gastric Absorption Study

The aim of this study was to assess the sublingual absorption of selegiline hydrochloride formulations according to Example 1. The pharmacokinetic profile of selegiline hydrochloride from the commercially available US tablet formulation should under the registered trademark Eldepryl® (available from Somerset Pharmaceuticals, Inc. 777 South Harbor Island Boulevard, Suite 880, Tampa Fla. 33602) served as a control for the degree of gastrointestinal absorption of selegiline. In addition, the study was designed to compare the urinary excretion over 24 hours of phenethylamine and 5-hydroxyindoleacetic acid (5-HIAA) from the subjects to whom such formulations had been administered.

This study was an open-labeled randomized 3-way crossover volunteer study and was performed as follows:

Eleven subjects of either sex aged between 45 and 62 years giving written informed consent underwent a thorough medical examination to establish their fitness to participate in the study. Subjects received each of the following treatments in the order dictated by a pre-determined randomization schedule:
1) 2×5 mg Eldepryl tablets taken with 150 ml water (Eldepryl (10 mg)).
2) 2×5 mg selegiline tablets produced according to Example 1 kept in the mouth for 1 minute and then expectorated and the mouth rinsed with 3×25 ml water and then expectorated (Example 1 (2.96 mg)).
3) 2×5 mg selegiline tablets produced according to Example 1 kept in the mouth for 1 minute and then swallowed (Example 1 (10 mg)).

Blood samples for determination of pharmacokinetic parameters were taken at baseline (immediately before drug administration) and then after 0.08, 0.16, 0.25, 0.5, 0.75, 1, 1.5, 2, 3, 4, 6 and 12 hours. Urine samples were taken immediately before drug administration and during the periods 0-2 hours, 2-4 hours, 4-6 hours, 6-12 hours and 12-24 hours.

Assays were performed to determine the concentration of selegiline in each of the blood plasma and urine samples and the concentration of phenethylamine and 5-hydroxyindoleacetic acid (5-HIAA) was measured in each of the urine samples. Selegiline was also measured in saliva and mouth washings.

Phenethylamine is the preferred substrate for monoamine oxidase B (MAO-B) and consequently its excretion has been shown to rise when MAO-B is inhibited. 5-HIAA is a breakdown product formed by the action of MAO-A on 5-hydroxytryptamine (serotonin). When MAO-A is inhibited, the 5-HIAA level excreted has been shown to decline.

Results

Figure 5:
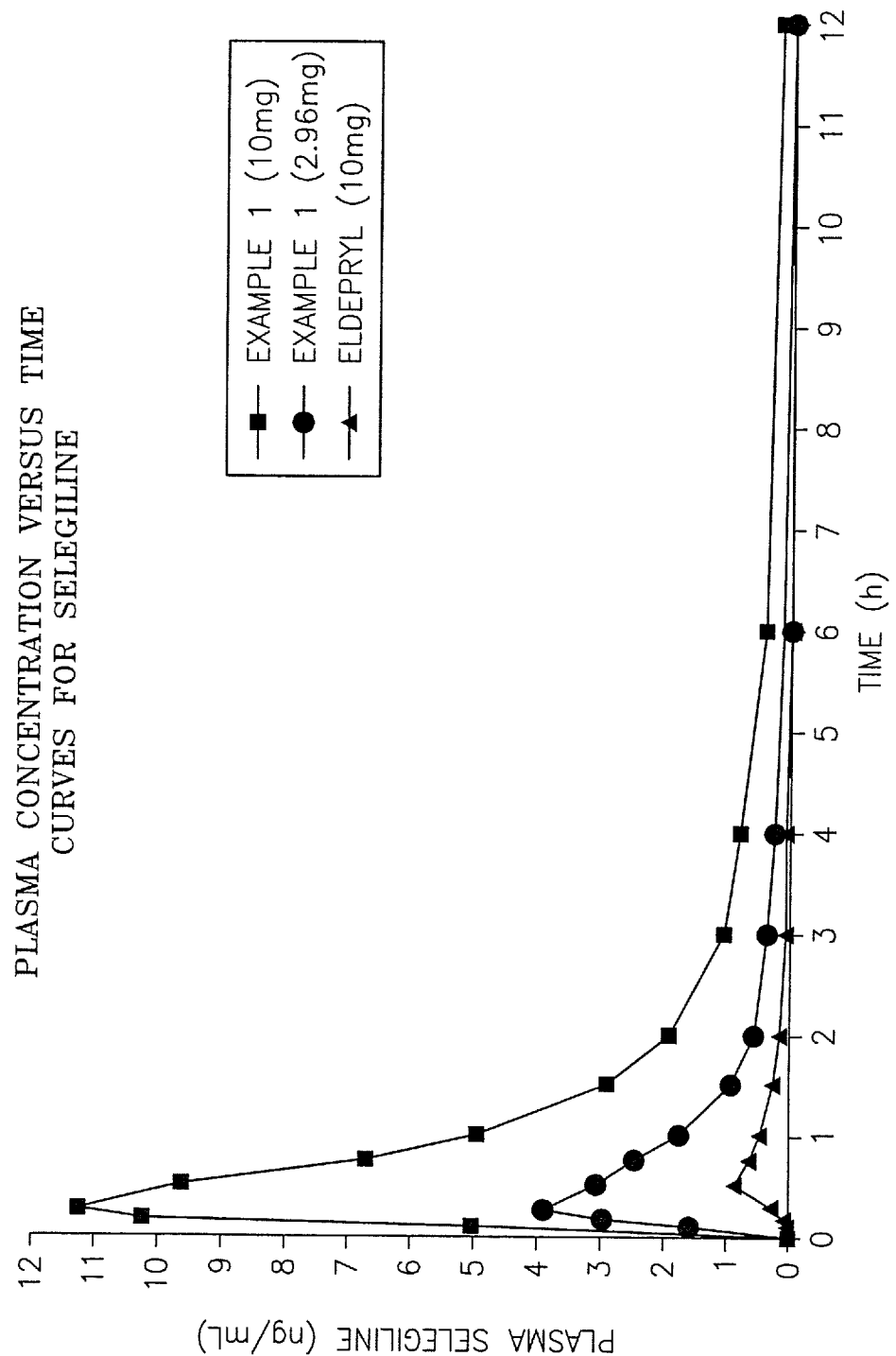
FIG. 5 is a graph of comparative concentration of selegiline in a blood plasma sample versus time for expectorated Example 1 formulation, swallowed Example 1 formulation, and the Eldepryl® tablet.
Figure 6:
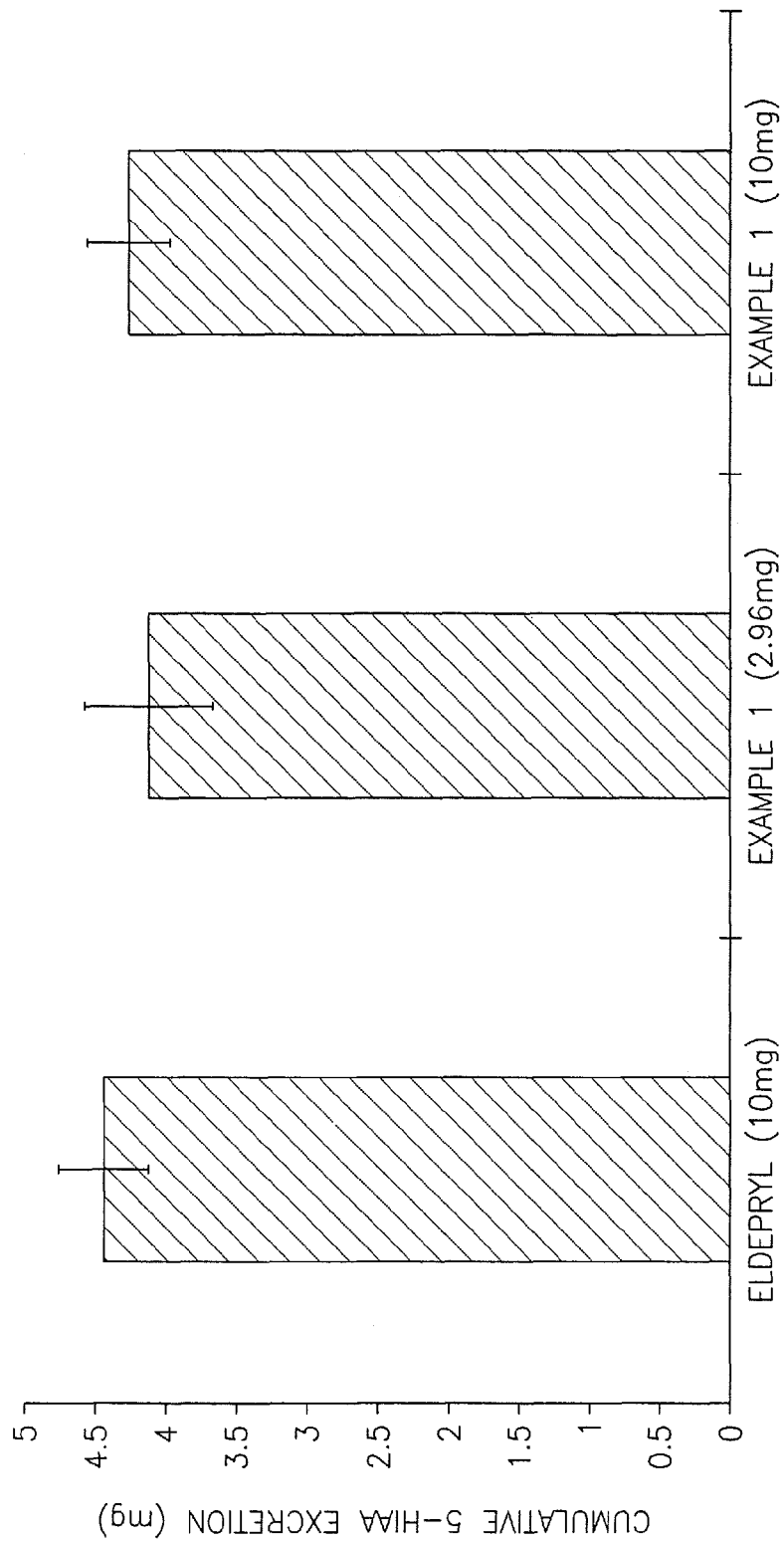
FIG. 6 is a chart showing comparative cumulative 5-hydroxyindoleacetic acid excretion in urine over 24 hours for the FIG. 5 samples.
Figure 7:
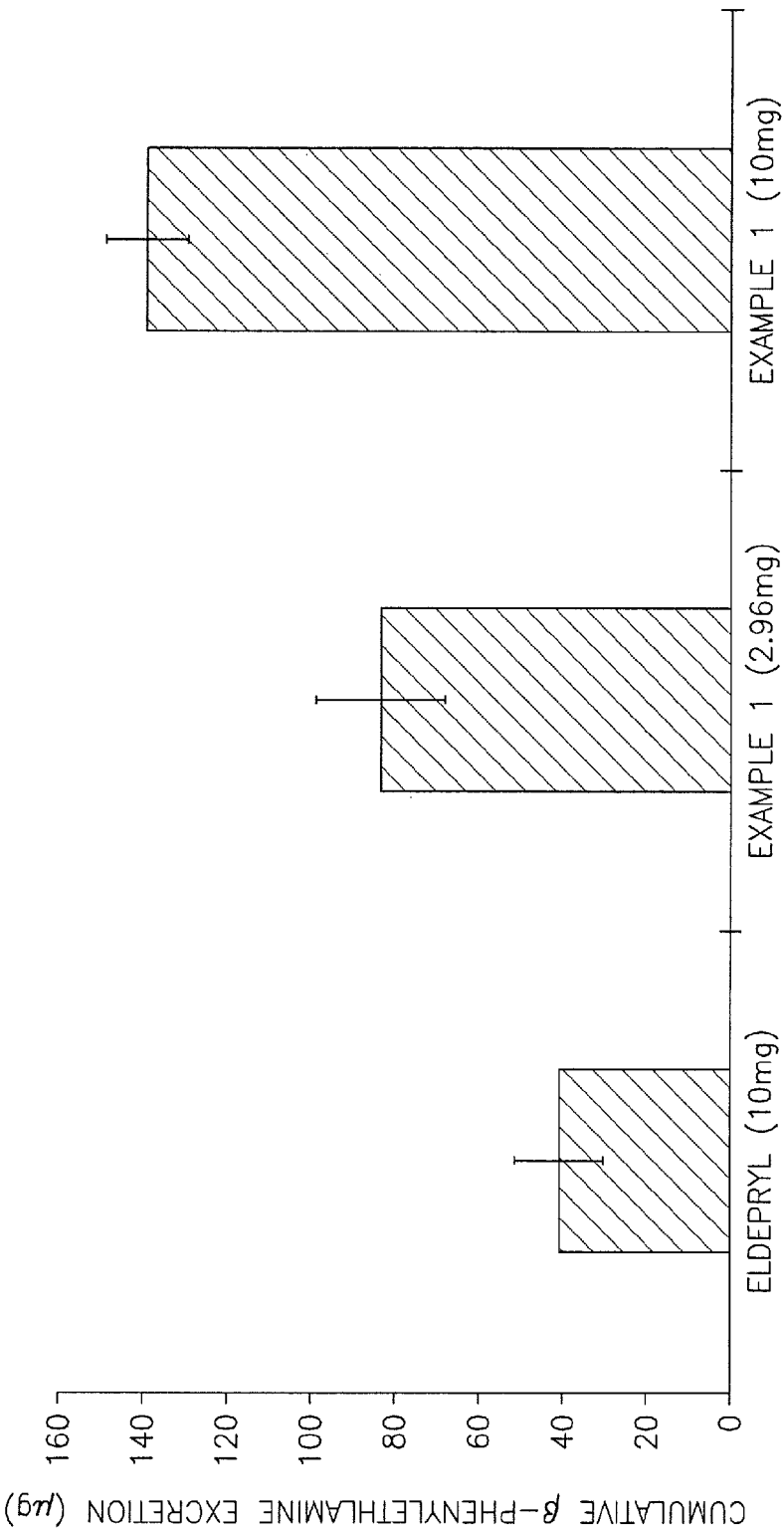
FIG. 7 shows the comparative cumulative phenethylamine excretion in urine over 24 hours for the FIG. 5 samples.

The results from the study are shown in graphical form in FIGS. 5, 6 and 7. When the tablets produced according to Example 1 were kept in the mouth for 1 minute and the saliva expectorated, an average concentration equivalent to 7.04 mg selegiline hydrochloride was measured in the mouth washings. Thus an average of 2.96 mg selegiline hydrochloride was absorbed pre-gastrically with this treatment. Subjects therefore received 2.96 mg, or 10 mg of selegiline hydrochloride from the 10 mg formulation produced according to Example 1 and 10 mg selegiline from the Eldepryl® formulation.

FIG. 5 is a plot of concentration of selegiline in a blood plasma sample versus the time at which the sample was taken for both expectorated and swallowed formulations of example 1 (Example 1 (equivalent to 2.96 mg) and Example 1 (10 mg) respectively) and the 10 mg tablet formulation sold under the trademark Eldepryl®. FIG. 6 shows the cumulative 5-hydroxyindoleacetic acid excretion in urine over 24 hours. FIG. 7 shows the cumulative phenethylamine excretion in urine over 24 hours.

From FIG. 5, it is apparent that the bioavailability of selegiline from both the 2.96 mg (expectorated) equivalent and 10 mg (swallowed) doses prepared according to Example 1 is much greater than that of selegiline from the Eldepryl® formulation, despite the fact that one formulation (Example 1 (10 mg swallowed)) contained the same amount of active ingredient as the Eldepryl® formulation and the expectorated treatment contained less than one third of the amount of active ingredient as the Eldepryl® formulation.

Moreover, it is apparent from FIG. 7 that this enhanced bioavailability is associated with a dose-related increase in the urinary excretion of phenethylamine. This was an unexpected result as increased phenethylamine excretion is caused by inhibition of monoamine oxidase B and it as hitherto believed that 10 mg of selegiline in standard tablet form (i.e., Eldepryl®) would be sufficient to cause maximal inhibition of monoamine oxidase B during the first 24 hours. In addition, the higher rate of excretion of phenethylamine in FIG. 7 for Example 1 (10 mg swallowed) and Example 1 (2.96 mg expectorated) than for the Eldepryl® formulation indicates a faster rate of monoamine oxidase B inhibition than with the former compositions and consequently a possible earlier alleviation of symptoms of Parkinson's disease, Alzheimer's disease and depression than for the Eldepryl® formulation.

Lack of inhibition of monoamine oxidase A by the Example 1 (10 mg swallowed) and Example 1 (2.96 mg expectorated) treatments was confirmed by analysis of the urine samples for concentration of 5-hydroxyindoleacetic acid, which is the metabolite of 5-hydroxutryptamine (serotonin) which is a principal substrate for monoamine oxidase A (see FIG. 6). Urinary concentrations of 5 hydroxyindoleacetic acid were similar for the Example 1 (10 mg swallowed), Example 1 (2.96 expectorated) and the standard Eldepryl tablet formulations, showing that the selegiline formulations produced according to Example 1 did not cause greater MAO-A inhibition than standard tablets despite the much increased selegiline bioavailability.

Once again, in view of the greater bioavailability of selegiline from the Example 1 (10 mg swallowed) and example 1 (2.96 expectorated) formulations, it is envisaged that the dose of selegiline could be significantly reduced thereby significantly reducing the quantity of unwanted metabolites with their associated side effects, while still achieving the desired therapeutic effects associated with inhibition of monoamine oxidase B.

The following examples further exemplify formulations which can be prepared using the process described in Example 1 which will promote pre-gastric absorption of selegiline and other MAO-B inhibitors:

Example 4 Fast Dispersing Oral Solid Dosage Formulation Containing Selegiline

| Ingredient | Weight (mg) | % by weight of composition |
|---|---|---|
| Purified water EP/USP* | 221.625 | 88.65 |
| Selegiline hydrochloride | 5.000 | 2.00 |
| Gelatin EP/USNF | 11.250 | 4.50 |
| Mannitol EP/USP | 8.125 | 3.25 |
| Aspartame EP/USNF | 1.250 | 0.50 |
| Grapefruit Flavor 502.106/A | 0.750 | 0.30 |
| Citric acid EP/USP | 1.250 | 0.50 |
| Opatint AD-22901 yellow | 0.750 | 0.30 |
| Total | 250.000 | 100.00 |

*signifies removed during the lyophilization process.

Example 5 Fast Dispersing Oral Solid Dosage Formulation Containing Selegiline

| Ingredient | Weight (mg) | % by weight of composition |
|---|---|---|
| Purified water EP/USP* | 224.125 | 89.65 |
| Selegiline hydrochloride | 5.000 | 2.00 |
| Gelatin EP/USNF | 9.375 | 3.75 |
| Mannitol EP/USP | 7.500 | 3.00 |
| Grapefruit Flavor 502.106/A | 0.750 | 0.30 |
| Citric acid EP/USP | 1.250 | 0.50 |
| Opatint AD-22901 yellow | 0.750 | 0.30 |
| Acesulfame K | 1.250 | 0.50 |
| Total | 250.000 | 100.00 |

*signifies removed during the lyophilization process.

Example 6 Fast Dispersing Oral Solid Dosage Formulation Containing Selegiline

| Ingredient | Weight (mg) | % by weight of composition |
|---|---|---|
| Purified water EP/USP* | 219.500 | 87.80 |
| Selegiline hydrochloride | 5.000 | 2.00 |
| Gelatin EP/USNF | 10.000 | 4.00 |
| Mannitol EP/USP | 7.500 | 3.00 |
| Aspartame EP/USNF | 1.000 | 0.40 |
| Glycine USP | 2.500 | 1.00 |
| Citric acid EP/USP | 1.250 | 0.50 |
| Opatint AD-22901 yellow | 0.750 | 0.30 |
| Lemon Lime flavor 59.15/AP | 2.500 | 1.00 |
| Total | 250.000 | 100.00 |

*signifies removed during the lyophilization process.

Example 7 Fast Dispersing Oral Solid Dosage Formulation Containing Selegiline

| Ingredient | Weight (mg) | % by weight of composition |
|---|---|---|
| Purified water EP/USP* | 223.625 | 89.45 |
| Selegiline hydrochloride | 5.000 | 2.00 |
| Gelatin EP/USNF | 10.000 | 4.00 |
| Mannitol EP/USP | 7.500 | 3.00 |
| Aspartame EP/USNF | 0.750 | 0.30 |
| Grapefruit Flavor 502.106/A | 0.750 | 0.30 |
| Citric acid EP/USP | 1.250 | 0.50 |
| Opatint AD-22901 yellow | 0.750 | 0.30 |
| Sodium methyl parabens EP/USNF | 0.250 | 0.10 |
| Sodium propyl parabens EP/USNF | 0.125 | 0.05 |
| Total | 250.000 | 100.00 |

*signifies removed during the lyophilization process.

Example 8 Fast Dispersing Oral Solid Dosage Formulation Containing Selegiline

| Ingredient | Weight (mg) | % by weight of composition |
|---|---|---|
| Purified water EP/USP* | 219.125 | 87.65 |
| Selegiline hydrochloride | 5.000 | 2.00 |
| Gelatin EP/USNF | 10.625 | 4.25 |
| Mannitol EP/USP | 6.875 | 2.75 |
| Aspartame EP/USNF | 1.250 | 0.50 |
| Glycine USP | 5.000 | 2.00 |
| Grapefruit Flavor 502.106/A | 0.750 | 0.30 |
| Citric acid EP/USP | 0.625 | 0.25 |
| Opatint AD-22901 yellow | 0.750 | 0.30 |
| Total | 250.000 | 100.00 |

*signifies removed during the lyophilization process.

Example 9 Fast Dispersing Oral Solid Dosage Formulation Containing Selegiline

| Ingredient | Weight (mg) | % by weight of composition |
|---|---|---|
| Purified water EP/USP* | 216.750 | 86.70 |
| Selegiline hydrochloride | 5.000 | 2.00 |
| Gelatin EP/USNF | 10.000 | 4.00 |
| Mannitol EP/USP | 7.500 | 3.00 |
| Aspartame EP/USNF | 1.250 | 0.50 |
| Glycine USP | 3.750 | 1.50 |
| Citric acid EP/USP | 1.250 | 0.50 |
| Opatint AD-22901 yellow | 0.750 | 0.30 |
| Acesulfame K | 1.250 | 0.50 |
| Lemon lime flavor 59.15/AP | 2.500 | 1.00 |
| Total | 250.000 | 100.00 |

*signifies removed during the lyophilization process.

Example 10 Fast Dispersing Oral Solid Dosage Formulation Containing Mofegiline

| Ingredient | Weight (mg) | % by weight of composition |
|---|---|---|
| Purified water EP/USP* | 215.875 | 86.35 |
| Mofegiline | 12.000 | 4.80 |
| Gelatin EP/USNF | 10.000 | 4.00 |
| Mannitol EP/USP | 8.125 | 3.25 |
| Aspartame EP/USNF | 1.250 | 0.50 |
| Grapefruit Flavor 502.106/A | 0.750 | 0.30 |
| Glycine USP | 1.250 | 0.50 |
| Opatint AD-22901 yellow | 0.750 | 0.30 |
| Total | 250.000 | 100.00 |

*signifies removed during the lyophilization process.

Example 11 Fast Dispersing Oral Solid Dosage Formulation Containing Lazabemide

| Ingredient | Weight (mg) | % by weight of composition |
|---|---|---|
| Purified water EP/USP* | 797.500 | 79.75 |
| Lazabemide | 100.000 | 10.00 |
| Gelatin EP/USNF | 45.000 | 4.50 |
| Mannitol EP/USP | 35.000 | 3.50 |
| Lemon lime flavor 59.15/AP | 5.000 | 0.50 |

-continued

| Ingredient | Weight (mg) | % by weight of composition |
|---|---|---|
| Glycine USP | 10.000 | 1.00 |
| Aspartame EP/USNF | 7.500 | 0.75 |
| Total | 1000.000 | 100.00 |

*signifies removed during the lyophilization process.

Additional clinical studies were performed pertaining to the therapeutic efficacy and safety of selegiline in the Zydis® (Cardinal Health, Inc., Dublin, Ohio) fast dispersing oral solid dosage form. The Zydis® fast-dispersing oral solid dosage form containing selegiline was prepared in a manner similar to that set forth in Example 1.

Example 12 Selegiline Inhibition of MAO-B

In four pharmacokinetic studies, the Log 10 AUC plasma selegiline was significantly correlated with the 24 hour cumulative urinary excretion of phenethylamine (PEA). By contrast, the same studies showed there was no significant correlation between Log 10 plasma N-desmethylselegiline (and therefore 1-amphetamine or 1-methamphetamine) and 24 hour phenethylemine excretion. This indicates that selegiline, and not its metabolites, was responsible for the MAO-B inhibition.

Figure 8:
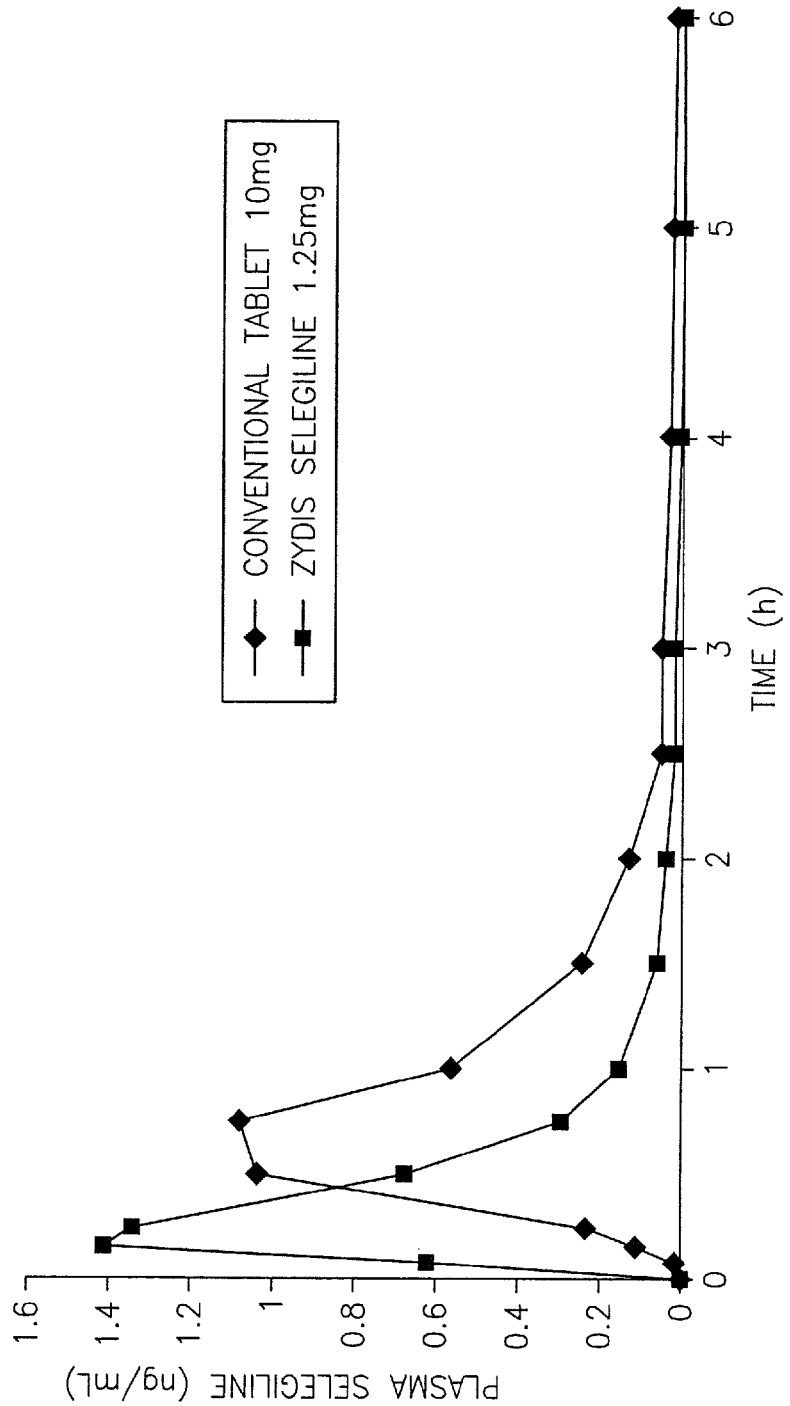
FIG. 8 is a graph containing plot data for measurements of plasma selegiline and 24 hour urinary excretion of phenethylamine.

The data from the studies is set forth in FIG. 8, which is a graph containing plot data for measurements of plasma selegiline and 24 hour urinary excretion of phenethylamine. Upon inspecting the graph, it can be clearly seen that there exists a remarkably consistent relationship between plasma selegiline concentrations and MAO-B inhibition, despite the route used to administer selegiline or at what dose.

Example 13 Comparative MAO-B Inhibition of Zydis® Selegiline and Commercial Selegiline Two studies were conducted using 1.25 mg doses of Zydis® fast dispersing oral solid selegiline dosage form. The first of these studies used a quartered Zydis selegiline 5 mg unit, with the remaining three-quarters made up with placebo to ensure a constant dosage of excipients. In the second study, Zydis selegiline 1.25 mg units were used. Again, cumulative urinary excretion of phenethylamine was measured over 24 hours for the 1.25 mg Zydis selegiline and 10 mg commercial selegiline tablets. As can be seen from the data in FIG. 9, the cumulative phenethylamine urinary excretion is similar. Therefore, it can be reasonably assumed that both formulations are equally efficacious despite the difference in dose amount. In other words, Zydis® fast dispersing solid oral dosage form for selegiline 1.25 mg is equally efficacious to the 10 mg commercial tablet.

Example 14 Selective Inhibition of MAO-B by Zydis Selegiline

An experiment to test for non-selective MAO inhibition was conducted using the oral tyramine pressor test. The oral tyramine pressor test is the clinically relevant model for detecting a lowering of the threshold of the cardiovascular effects of tyramine (i.e., "cheese reaction"). This test was therefore carried out before selegiline dosing and after treatment on day 14 in all 24 subjects used in the study. Of the 24 subjects, 12 received 10 mg Zydis® selegiline and 12 received 10 mg conventional selegiline.

A "survival-type" analysis was performed and the mean dose of tyramine (±SD) required to achieve the cardiovascular threshold after each treatment was determined, the mean doses as follows:

| | |
|---|---|
| Conventional tablet control | 400 mg (73.9) |
| Conventional selegiline | 131.3 mg (65.0) |
| Zydis control | 408.3 mg (131.1) |
| Zydis selegiline | 120.8 mg (49.8) |

From this mean (±SD) the tyramine pressor endpoint ratio for 10 mg Zydis® selegiline was calculated to be 3.67 (1.3) and the ratio for 10 mg conventional selegiline was calculated to be 4.5 (4.1). Thus, as far as the effects on MAO-A were concerned, 10 mg Zydis® selegiline was equivalent to 10 mg of conventional selegiline tablets. These ratios were also in close agreement with the observations of others (Table 2) and showed that both treatments had similar and probable minimal or no effects on MAO-A. Further as a result, no new safety concerns had emerged from the repeated use of 10 mg Zydis® selegiline over those from the use of 10 mg conventional selegiline. If MAO-A been fully inhibited, the tyramine pressor endpoint ratio would have been expected to exceed 20.

TABLE 2

Tyramine Pressor Endpoint Ratios for Selegiline Doses Over 2-3 Weeks

| Selegiline daily dose mg (n) | Tyramine Pressor Endpoint Ratio (Tyramine route) |
|---|---|
| 5 (8) | 1.7 (oral) |
| 5 (8) | 2.8 (oral) |
| 10 (7) | 3.7 (i.v.) |
| 10 (2) | 1.7 (i.v.i) |
| 15* (4) | 2.1 (i.v.) |
| 20 (7) | 3.8 (oral) |
| 20 (7) | 4.5 (oral) |
| 30** (7) | 3.1 (oral) |

*indicates ascending dose over 3 weeks (5-15 mg)
**indicates ascending dose over 1 week (5030 mg)
i.v.i. indicates intravenous infusion The results demonstrate that despite higher concentrations of unchanged selegiline occurring in plasma after 10 mg Zydis® selegiline compared with 10 mg conventionally administered selegiline, the MAO-B selectivity had been retained. The fact that the tyramine pressor endpoint ratio was similar for tyramine given orally or intravenously strongly suggests that gastro-intestinal MAO-A inhibition played little part in the change of threshold, and that the potentiation of tyramine was brought about by intravascular actions, possibly through platelet MAO-B inhibition, although an effect on MAO-A in sympathetic nerve endings cannot be eliminated. Accordingly, it is reasonable to assume that the chance of non-selectivity occurring with Zydis® selegiline 1.25 mg is very small.

Example 15 Comparative MHPG Plasma Levels

Figure 10:
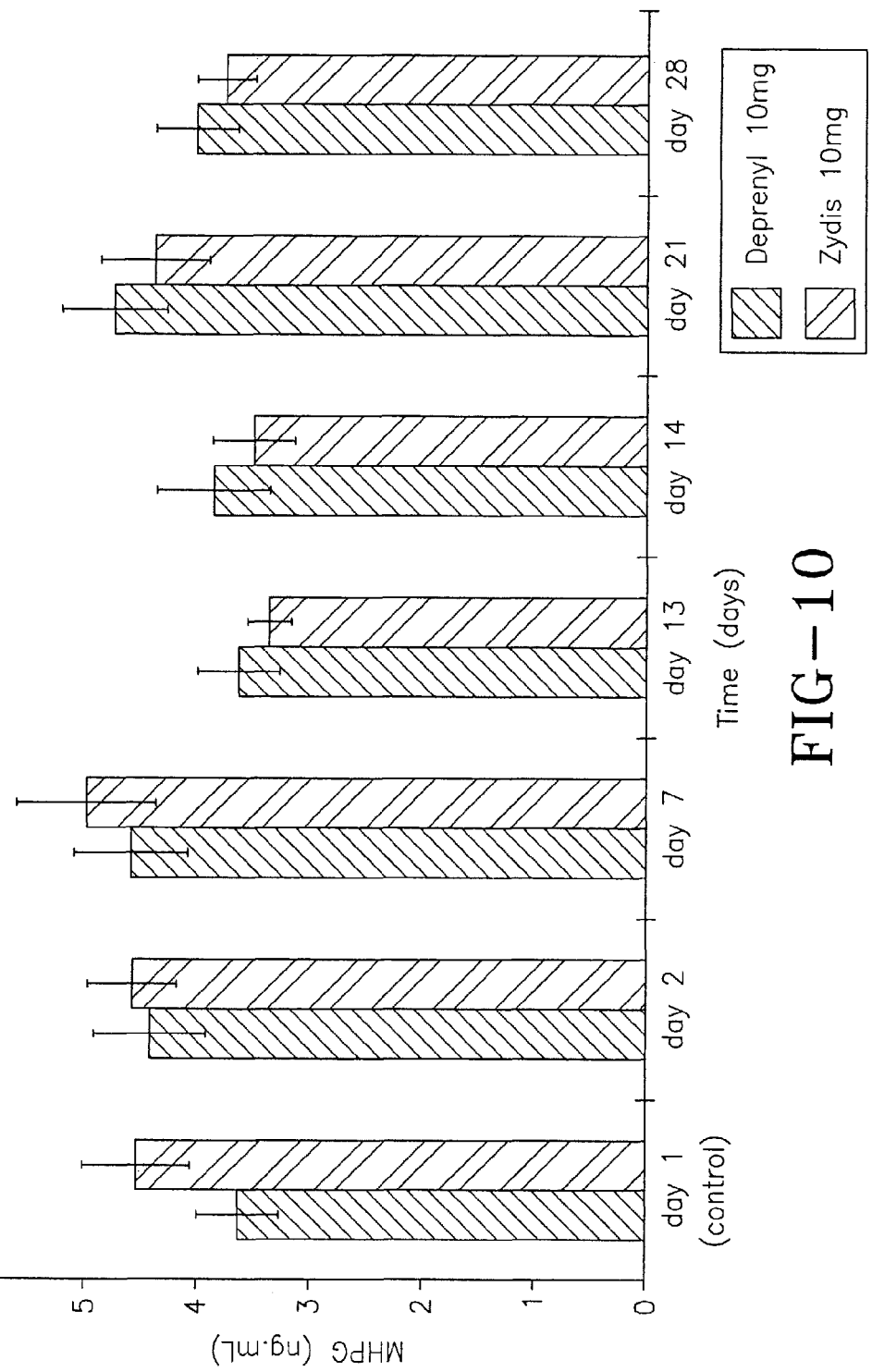
FIG. 10 is a graph showing comparative pre-dose plasma levels over time for Zydis® selegiline and conventional selegiline.

In another study, plasma MHPG was measured at baseline and 24 hours following treatment using 10 mg Zydis® selegiline and conventional selegiline (Deprenyl®) at intervals over 28 days. The results are shown in FIG. 10. As can be seen from the data in FIG. 10, changes in pre-dose MHPG plasma levels varied over the 4 week period, but the effects of both treatments were identical—not only with respect to change over time, but also that there was no statistically significant difference between 10 mg Zydis® selegiline and conventional selegiline at any time point. As can be seen from the graph, the measurement of plasma MHPG concentrations reveal minimal inhibition of MAO-A with 10 mg of either Zydis® selegiline or conventional selegiline.

Reference has been made herein above to the content of certain documents in the course of describing the invention. The full texts of each such cited reference are incorporated herein by reference. The invention has been described herein above with reference to various and specific embodiments and techniques. It will be understood by one of ordinary skill in the art, however, that reasonable modifications and variations can be made from such embodiments and techniques while remaining within the spirit and scope of the invention defined by the following claims.

What is claimed is:

1. A fast disintegrating oral solid dosage form formulated for pre-gastric absorption, the dosage form consisting essentially of selegiline as the active ingredient and comprising selegiline and a carrier in a freeze-dried form having a porous network structure.

2. The fast disintegrating oral solid dosage form according to claim 1, wherein the dosage form is formulated to promote absorption of the selegiline through the buccal, sublingual, pharyngeal or esophageal mucous membrane.

3. The fast disintegrating oral solid dosage foil ii according to claim 1, wherein the dosage form disintegrates within one minute after placement in the oral cavity.

4. The fast disintegrating oral solid dosage form according to claim 3, wherein the dosage form disintegrates within 10 seconds after placement in the oral cavity.

5. The fast disintegrating oral solid dosage form according to claim 1, wherein at least 5% of the selegiline is absorbed within one minute of placement in the oral cavity as measured by a buccal absorption test.

6. The fast disintegrating oral solid dosage form according to claim 5, wherein at least 10% of the selegiline is absorbed within one minute of placement in the oral cavity as measured by a buccal absorption test.

7. The fast disintegrating oral solid dosage form according to claim 6, wherein at least 15% of the selegiline is absorbed within one minute of placement in the oral cavity as measured by a buccal absorption test.

8. The fast disintegrating oral solid dosage form according to claim 1, wherein the dosage form is formulated such that about 2.96 mg of selegiline hydrochloride is pre-gastrically absorbed within one minute of placement in the oral cavity.

9. The fast disintegrating oral solid dosage form according to claim 1, wherein the bioavailability of the selegiline is at least 8 times that as compared to an orally swallowed solid tablet dosage form, wherein each of the dosage forms contain the same amount of selegiline.

10. A fast disintegrating oral solid dosage form for the treatment of a subject having Parkinson's disease consisting essentially of selegiline or a salt thereof or a combination thereof as the active ingredient, and one or more matrix forming agents, in a freeze dried form having a porous network structure, whereby the selegiline is absorbed through the pre-gastric mucosa of the subject when the solid dosage form is placed into the oral cavity.

11. The fast disintegrating oral solid dosage form according to claim 10, wherein the dosage form is formulated to promote absorption of the selegiline through the buccal, sublingual, pharyngeal or esophageal mucous membrane.

12. The fast disintegrating oral solid dosage form according to claim 10, wherein the dosage form disintegrates within one minute after placement in the oral cavity.

13. The fast disintegrating oral solid dosage form according to claim 12, wherein the dosage form disintegrates within 1 to 10 seconds after placement in the oral cavity.

14. The fast disintegrating oral solid dosage form according to claim 10, wherein at least 5% of the selegiline is absorbed within one minute of placement in the oral cavity as measured by a buccal absorption test.

15. The fast disintegrating oral solid dosage form according to claim 14, wherein at least 10% of the selegiline is absorbed within one minute of placement in the oral cavity as measured by a buccal absorption test.

16. The fast disintegrating oral solid dosage form according to claim 15, wherein at least 15% of the selegiline is absorbed within one minute of placement in the oral cavity as measured by a buccal absorption test.

17. The fast disintegrating oral solid dosage form according to claim 10, wherein the dosage form is formulated such that about 2.96 mg of selegiline hydrochloride is pre-gastrically absorbed within one minute of placement in the oral cavity.

18. The fast disintegrating oral solid dosage form according to claim 10, wherein the bioavailability of the selegiline is at least 8 times that as compared to an orally swallowed solid tablet dosage form, wherein each of the dosage forms contain the same amount of selegiline.

* * * * *